United States Patent [19]

Brooks et al.

[11] Patent Number: 4,636,496
[45] Date of Patent: Jan. 13, 1987

[54] COMPOSITIONS INHIBITING MURINE MXT DUCTAL CARCINOMA

[75] Inventors: Samuel C. Brooks, Orchard Lake; Jerome P. Horwitz, Oak Park, both of Mich.

[73] Assignee: Wayne State University, Detroit, Mich.

[21] Appl. No.: 823,273

[22] Filed: Jan. 28, 1986

Related U.S. Application Data

[63] Continuation-in-part of Ser. No. 741,125, Jun. 4, 1985, which is a continuation of Ser. No. 591,500, Mar. 20, 1984, Pat. No. 4,568,673.

[51] Int. Cl.$^4$ ............................................. A61K 31/56
[52] U.S. Cl. ................................. 514/182; 260/397.5
[58] Field of Search .......................... 514/178, 182; 260/397.5

[56] References Cited

U.S. PATENT DOCUMENTS

| 3,377,362 | 4/1968 | Cantrall et al. | 260/397.4 |
| 3,526,648 | 9/1970 | Bertin et al. | 260/397.45 |
| 4,340,602 | 7/1982 | Brooks | 514/182 |
| 4,496,555 | 1/1985 | Brooks et al. | 260/397.5 |

OTHER PUBLICATIONS

Rozhin et al., Cancer Res., 43:2611–2617, (Jun., 1983).
Rozhin et al., Proc. Am. Assoc. Cancer Res., 21:260, (1980).
Neeman et al., J. Med. Chem., 1983:465–469, (1983).
Utne et al., J. Org. Chem., 33:2469–2473, (1968).
Iyer et al., J. Org. Chem., 47:644, (1982).
Iyer et al., J. Med. Chem., 28:162, (1983).
Brooks et al., J. Toxic. and Environ. Health, 4:283–300, (1978).
Rozhin et al., J. Biol. Chem., 252:7214–7220, (1977).
Pack et al., Endocrinology, 95:1680–1690, (1974).

Primary Examiner—Elbert L. Roberts
Attorney, Agent, or Firm—John S. Roberts, Jr.

[57] ABSTRACT

A compound of the formula

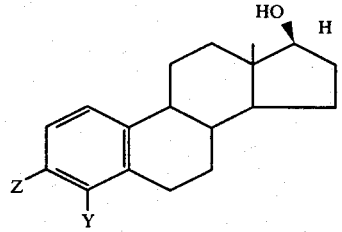

wherein Z is hydrogen and Y is nitro, inhibits the growth of murine ductal carcinoma (MXT mammary tumors).

7 Claims, No Drawings

COMPOSITIONS INHIBITING MURINE MXT DUCTAL CARCINOMA

REFERENCE TO RELATED APPLICATIONS

This application is a continuation in part of Brooks, et al., Ser. No. 741,125, filed June 4, 1985, which is a continuation of Brooks, et al., Ser. No. 591,500, filed Mar. 20, 1984, now U.S. Pat. No. 4,568,673.

BACKGROUND OF THE INVENTION

This invention relates to the inhibition of hormone-dependent mammary tumors, such as those induced by 7,12-dimethylbenz(a)anthracene or transplantable ductal carcinoma (MXT murine type), by compounds known to be inhibitors of estrogen sulfotransferase.

Estrogen sulfotransferase inhibitors, such as 4-nitroestrone 3-methyl ether, are expected to prevent implantation of a blastocyst in the epithelial uterine lining of a pregnant female. Accordingly, these compounds may function as contragestative agents, Brooks U.S. Pat. No. 4,340,602.

Brooks, et al, U.S. Pat. No. 4,496,555, have further disclosed fluoro, amino, nitro and hydroxy-substituted compounds, which inhibit estrogen sulfotransferase activity.

A member of this group of compounds, 4-nitroestrone 3-methyl ether also has been found to inhibit the growth of hormone dependent mammary tumors, induced by 7,12-dimethylbenz(a)anthracene, Rozhin et al., *Proc. Am. Assoc. Cancer Res.*, 21:260 (1980). It has been found that the utility of 4-nitroestrone 3-methyl ether is essentially limited to parental administration, particularly intraperitoneal or subcutaneous injection thereof.

It is an object of this invention to provide compounds which are active against hormone-dependent mammary tumors, other than those induced by 7,12-dimethylbenz-(a)anthracene, and to provide compounds which are active when administered orally.

PRIOR ART STATEMENT

Brooks, in U.S. Pat. No. 4,340,602, herein incorporated by reference, has proposed that derivatives of 2- and/or 4-bromo- or nitroestradiol or estrone, having an etherified hydroxyl function at the 3-position are active inhibitors of estrogen sulfotransferase activity. The active compounds should act to prevent implantation of a blastocyst in the epithelial uterine lining of a female mammal.

Brooks et al., U.S. Pat. No. 4,496,555, herein incorporated by reference, have proposed that deoxyestrone or deoxyestra-17-ols, substituted at either the 2- or 4-position by amino, nitro, fluoro or hydroxy, are useful as estrogen sulfotransferase inhibitors.

Cantrall et al., U.S. Pat. No. 3,377,362, indicate that 1-halo-3-methoxy-estra-1,3,5(10)-triene-17-one and related compounds have estrogenic, hypocholesteremic and protein anabolic activity.

Δ1,3,5(10)-Gonatrienes having an 11 betaalkoxy substituent, wherein the 2-substituent is H, halogen or methyl; the 3-substituent is H, alkoxy or acyloxy; the 4-substituent is H, halo or lower alkyl; and the 17-substituent is =O or

are disclosed by Bertin et al., U.S. Pat. No. 3,526,648, as having estrogenic activity.

Pertinent literature references include:

Rozhin et al., "Effects of 4-Nitroestrone 3-Methyl Ether on Dimethylbenz(a)anthracene-induced Mammary Tumors," *Cancer Res.*, 43:2611–2617 (June, 1983).

Rozhin et al., "Effect of an Inhibitor of Estrogen Sulfurylation, 4-Nitroestrone 3-Methyl Ether on Mammary Tumor Growth," *Proc. Am. Assoc. Cancer Res.*, 21:260 (1980).

Neeman et al., "Modified Steroid Hormones. 7. 4-Fluoro-17 beta-estradiol: Carbon-13 Nuclear Magnetic Resonance, Crystal and Molecular Structure, and Biological Activity," *J. Med. Chem.*, 1983:465–469 (1983).

Utne et al., "The Synthesis of 2- and 4-Fluoroestradiol," *J. Org. Chem.*, 33:2469–2473 (1968).

Iyer et al., *J. Org. Chem.*, 47:644 (1982) and *J. Med. Chem.*, 28:162 (1983).

Brooks et al., "Role of Sulfate Conjugation in Estrogen Metabolism and Activity," *J. Toxic. and Environ. Health*, 4:283–300 (1978).

Rozhin et al., "Studies on Bovine Adrenal Estrogen Sulfotransferase: II. Inhibition and Possible Involvement of Adenine-estrogen Stacking," *J. Biol. Chem.*, 252:7214–7220 (1977).

Pack et al., "Cyclic Activity of Estrogen Sulfotransferase in the Gilt Uterus," *Endocrinology*, 95:1680–1690 (1974).

SUMMARY OF THE INVENTION

This invention relates to a composition which inhibits the growth of hormone dependent MXT mammary tumors, comprising a compound of the formula

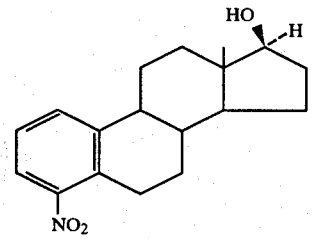

in admixture with a pharmaceutically acceptable carrier.

This invention further relates to a method of inhibiting the growth of MXT murine ductal carcinoma by administering to mice being treated an amount of the foregoing compound, effective to inhibit growth of MXT ductal carcinoma.

This invention further relates to improved methods for the synthesis of 2- or 4-substituted estra-1,3,5(10)-trien-17-beta-ols, of which 4-nitroestra-1,3,5(10)-trien-17-beta-ol is shown to inhibit the growth of murine MXT mammary ductal carcinoma. The compounds are active as inhibitors of estrogen sulfotransferase.

The active compounds can be represented by the formula

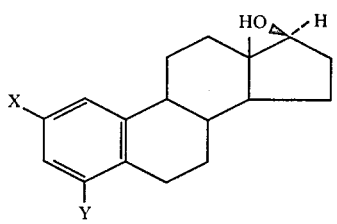

wherein X or Y is hydrogen, halogen, nitro, amino or hydroxy, provided that one of X or Y is other than hydrogen and the other is hydrogen.

Synthesis and Evaluation Section

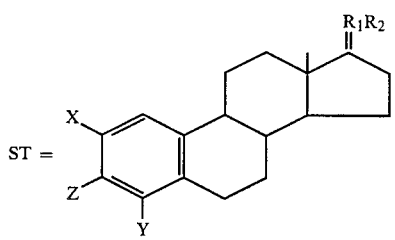

In the specification, ST represents an estra-1,3,5(10)-triene residue and substitutents X, Y, Z, $R_1$, and $R_2$ are as indicated in each case.

This invention further relates to a process for the synthesis of 2- or 4-substituted estra-1,3,5(10)-trien-17 beta-ols by the steps of:

(a) converting a precursor 2- or 4-nitroestrone (ST; X or Y is $NO_2$, Z is OH, $R_1+R_2$ is =O) to a corresponding 2- or 4-nitroestrone 3-O-(trifluoromethyl)sulfonate (ST; X or Y is $NO_2$, Z is $OSO_2CF_3$, $R_1+R_2$ is =O);

(b) reducing the thus-produced 2- or 4-nitroestrone 3-O-(trifluoromethyl)sulfonate to a corresponding 2- or 4-nitroestra-1,3,5(10)-trien-3,17-beta-diol 3-O-(trifluoromethyl)sulfonate (ST; X or Y is $NO_2$; Z is $OSO_2CF_3$; $R_1$ is beta-OH and $R_2$ is H) with sodium borohydride in the presence of a phase transfer agent;

(c) hydrogenating the thus-produced 2- or 4-nitroestra-1,3,5(10)-3,17-beta-diol 3-O-(trifluoromethyl)sulfonate to a corresponding 2- or 4-amino-1,3,5(10)-trien-17-beta-ol by catalytic hydrogenation and, when the 2- or 4-substituent is other than amino, including the further step of:

(d) converting the thus-formed 2- or 4-aminoestra-1,3,5(10)-trien-17-beta-ol to a corresponding 2- or 4-haloestra-1,3,5(10)-trien-17-beta-ol by formation of a diazonium salt and treatment with a cuprous salt or (e) converting the thus-formed 2- or 4-aminoestra-1,3,5(10)-trien-17-beta-ol by oxidation with meta-chloroperbenzoic acid (MCPBA).

A contemplated equivalent of step (d) is conversion to a 2- or 4-fluoro compound by reaction with a diazonium fluoborate.

A readily separable mixture of 2- and 4-nitroestrone is obtained by nitration of estrone (ST; Z=OH, $R_1+R_2$=O) with a stoichiometric amount of nitric acid in glacial acetic acid. See, generally, Werbin et al., *J. Biol. Chem.*, 223:651 (1965); Krachy, et al., *J. Am. Chem. Soc.*, 79:754 (1957); Pickering, et al., *Ibid*, 80:680 (1958); and Tomson, et al., *J. Org. Chem.*, 24:2056 (1959).

4-Aminoestra-1,3,5(10)-trien-17-beta-ol was synthesized, starting from 4-nitroestrone. This was converted to 4-nitroestrone 3-O-(trifluoromethyl)sulfonate (ST; Z=$CF_3SO_2O$, Y—$NH_2$, $R_1$=17 beta-OH, $R_2$=H), which was treated with hexadecyltributylphosphonium bromide/sodium borohydride to give 4-nitroestra-1,3,5(10)3,17-beta-diol 3-O-(trifluoromethyl)sulfonate (ST; Z=$CF_3SO_2O$, Y=$NO_2$, $R_1$=17 beta-OH) and reduced by hydrogenation.

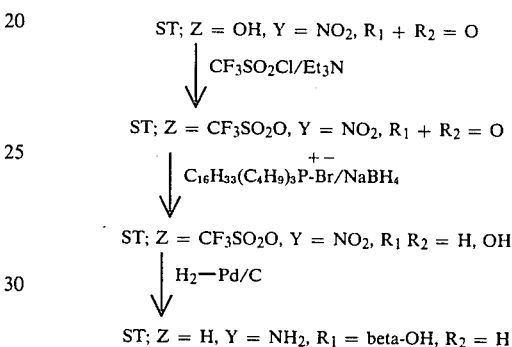

Phenyl trifluoromethanesulfonates are disclosed by Yagupol'skii et al., "Aryl Trifluoromethanesulfonates," Institute of Organic Chemistry, Academy of Sciences of the Ukranian SSR. Translated from *Zhurnal Organicheskoi Khimii*, 7:996–1001 (1971). Hydrogenolysis of phenol or enols using perfluorosulfonates is shown by L. R. Subramanian et al., "Perfluoroalkane Sulfonic Esters, Methods of Preparation and Applications in Organic Chemistry," *Synthesis*, 85–125 (1982).

Catalytic reduction can be done by the method of Tomson et al., supra, or that of Utne et al., supra. Chemical reduction can be done according to Kratchy et al., supra.

The Sandmeyer reaction can be done in accordance with Tomson et al., supra, or Sweet et al, *J. Med. Chem.*, 44:2296 (1979). This reaction accomplishes conversion of an aromatic amine to a halogen compound by formation of a diazonium salt and treatment of the thus-formed diazonium salt with a cuprous halide or by direct treatment with a diazonium fluoborate.

In reduction of the 17-keto function of estrone using sodium borohydride, the phase transfer agent is selected from tetraalkyl phosphonium halides, particularly the bromides. A most preferred phase transfer agent is hexadecyltributylphosphonium bromide.

Catalytic reduction of the 2- or 4-nitro function is preferably done in the presence of a supported catalyst, most preferably palladium on carbon.

Further conversions of 4-aminoestra-1,3,5(10)-trien-17-beta-ol can be represented by the equations:

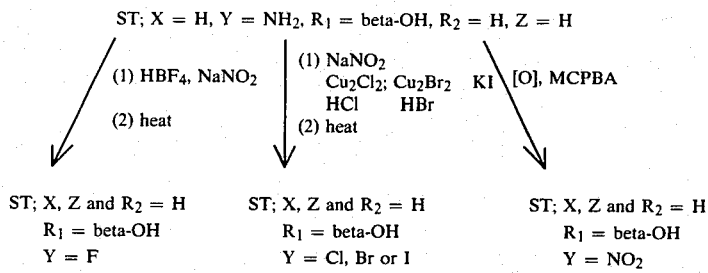

It will be understood that 2-substituted estra-1,3,5(10)-trien-17-beta-ols are synthesized in a similar fashion, starting from 2-nitroestrone.

The compounds of this invention were evaluated for inhibitory activity against murine hormone-dependent mammary tumors of the MXT type or of the type induced by 7,12-dimethylbenz(a)anthracene by methods cited above.

Due to their tumor inhibiting activity, the compounds of this invention are useful for treating hormone-dependent mammary tumors in human and veterinary medicine.

The compounds of this invention can be employed in admixture with conventional excipients, i.e., pharmaceutically acceptable organic or inorganic carrier substances suitable for parenteral, enteral or topical application, which do not deleteriously react with the active compounds.

Suitable pharmaceutically acceptable carriers include but are not limited to water, salt solutions, alcohols, vegetable oils, polyethylene glycols, gelatine, lactose, amylose, magnesium stearate, talc, silicic acid, viscous parafin, perfume oil, fatty acid monoglycerides and diglycerides, pentaerythritol fatty acid esters, hydroxymethyl cellulose, polyvinyl pyrrolidone, etc.

The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substance, which do not deleteriously interact with the active compounds.

For parenteral application, solutions are particularly suitable, including oily or aqueous solutions, suspensions, emulsions, implants or suppositories. Ampoules are convenient unit dosages.

It will be understood that preferred dosages of the active compounds used will vary according to the specific compound being used, the particular compositions formulated, the mode of application, and the particular organism being treated. Optimal application rates for a given set of conditions can be ascertained by those skilled in the art using conventional dosage determination tests in view of the above guidelines.

DESCRIPTION OF MOST PREFERRED EMBODIMENT

In a most preferred embodiment, 4-nitroestro-1,3,5(10)-trien-17-beta-ol will be administered subcutaneously.

Without further elaboration, it is believed that one skilled in the art can, using the preceding description, utilize the present invention to its fullest extent. The following preferred specific embodiments are therefore to be construed as merely illustrative and not limitative of the remainder of the specification and claims in any way whatsoever.

Infrared spectra were recorded on a Perkin Elmer Model 1330 spectrophotometer. $^1$H NMR spectra were obtained with JEOL FX 100 and Nicolet QE 300 FT spectrometers in CDCl$_3$ and are reported in parts per million downfield from internal (CH$_3$)$_4$Si. Electron-impact mass spectra were determined by direct insertion probe with a Finnegan Model 4000 instrument.

Elemental analyses were performed by M-H-W Laboratories, Phoenix, AZ. Melting points were obtained on a Thomas-Hoover capillary meeting point apparatus and are uncorrected. All solvent evaporations were carried out under reduced pressure in a Buchi rotoevaporator. Flash chromatography utilized E. Merck (40–63 micrometers) silica gel. TLC was carried out with a pre-coated silica gel F-254 on aluminum foil in the following solvents: S$_1$, CH$_2$Cl$_2$; S$_2$, ethyl ether/CH$_2$Cl$_2$, 5/95; S$_3$, EtOAC/toluene, 5/95.

EXAMPLE 1

4-Nitroestrone 3-O-(Trifluoromethyl)sulfonate

To a solution of 4-nitroestrone (630 mg, 2 mmol) in 50 ml dry acetone containing 350 ml (2.5 mmol) of triethylamine was added 265 ml (2.5 mmol) of trifluoromethanesulfonyl chloride and the reaction mixture, protected from moisture, was heated under reflux for 3 hr. The solvent was evaporated to dryness and residue was dissolved in 100 ml of dichloromethane. The solution was washed and dried over sodium sulfate. The filtered solution was evaporated to dryness and the residue, 4-nitroestrone-3-O-(trifluoromethyl)sulfonate, which had a single spot on TLC using 99% dichloromethane-1% methanol, was crystallized from 2-propanol in the form of yellow needles, wt. 700 mg, (78% yield), mp 198°–202° C. Ir (KBr) cm$^{-1}$ 1740 (C$_{17}$ C=O), 1545, 1370 (NO$_2$), 1430, 1220 (—OSO$_2$—). $^1$H NMR 7.53, 7.28 (dd, 2, aromatic H$_1$, H$_2$), 3.00–1.2 (m, 15), 0.93 (s, 3, C$_{18}$CH$_3$).

Anal. Calc'd. for C$_{19}$H$_{20}$NO$_6$SF$_3$: C, 51.00; H, 4.51; N, 3.13; S, 7.17; F, 12.74. Found: C, 51.13; H, 4.66; N, 3.03, S, 6.93; F, 12.56.

EXAMPLE 2

4-Nitroestra-1,3,5(10)-triene-3,17-beta-diol-3-O-(Trifluoromethyl)-Sulfonate

To a solution of 230 mg (0.5 mmol) of 4-nitroestrone 3-O-(trifluoromethyl)sulfonate in 230 ml of toluene, containing hexadecyltributylphosphonium bromide (26 mg, 0.05 mmol) was slowly added a solution of sodium borohydride (60 mg 1.5 mmol) in 150 ml of water and the resulting mixture was stirred at room temperature for 3 hr. Additional (10 ml) toluene was added and the organic layer was separated and then washed with water. The toluene solution was dried over sodium sulfate and then evaporated to an oily residue. This gave a colorless foam of 4-nitroestra-1,3,5(10)-trien-3,17-beta-diol 3-O-(trifluoromethyl)sulfonate (184 mg, 82% yield) on evaporation from ether. Ir (KBr) cm$^{-1}$ 1540, 1365 (NO$_2$), 1430, 1230 (—OSO$_2$—). $^1$H NMR $\delta$7.52, 7.26, (dd, 2, aromatic H$_1$, H$_2$), 3.68 (t, 1.17 H), 2.88–1.28 (m 16), 0.80 (s, 3, C$_{18}$CH$_3$).

Anal. Calc'd. for C$_{19}$H$_{22}$NO$_6$SF$_3$: C, 50.77; H, 4.93; N, 3.12; S, 7.14; F, 12.68. Found: C, 50.58; H, 5.03; N, 3.00; S, 6.95; F, 12.79.

EXAMPLE 3

4-Aminoestra-1,3,5(10)-trien-17-beta-ol

A solution of 4-nitroestra-1,3,5(10)-trien-3,17-beta-diol 3-O-(trifluoromethyl)sulfonate (2.13 g, 4.74 mmol) in 100 ml of methanol containing triethylamine (6.60 L, 4.8 mmol) and 10% Pd/C (430 mg. 20% by weight) was hydrogenated in a Parr apparatus at 16 psi for 5 hr. TLC using 95% dichloromethane 1% methanol showed one major product and 3 minor constituents. The reaction mixture was filtered through Celite and the filtrate was evaporated to dryness. The residue was dissolved in excess dichloromethane and the solution was washed with water. The extract was dried over sodium sulfate and filtered. The filtrate was evaporated to dryness. The residue crystallized from methanol as a cluster of colorless needles of 4-aminoestra-1,3,5(10)-trien-17-beta-ol; wt. 320 mg. (25% yield), mp 189°-192° C. Mass Spectrum: m/z 271 (M+), 237 (M—H$_2$O+NH$_2$). $^1$H NMR 7.23–6.51 (m, 3, H$_1$, H$_2$, H$_3$ aromatic) 3.71–3.45 (t, 1, 17 H), 2.57–1.23 (m, 18), 0.76 (s, 3, C$_{18}$CH$_3$).

Anal. Calc'd. for C$_{18}$H$_{25}$NO: C, 79.66; H, 9.28; N, 5.16. Found: C, 79.72; H, 9.11; N, 4.97.

EXAMPLE 4

4-Fluoroestra-1,3,5(10)-trien-17-beta-ol

A solution of (230 mg, 0.85 mmol) 4-aminoestra-1,3,5(10)-trien-17-beta-ol in 4.6 ml of ethanol containing 2.3 ml of 48% hydrofluoroboric acid, was cooled to 0° C. and maintained at this temperature with stirring during dropwise addition of an aqueous solution (230 ml) of sodium nitrite (60 mg, 0.88 mml). After 1 hr. of stirring at 0°, the reaction mixture was first treated with a few crystals of urea and then poured into 150 ml of ether. The product, a colorless solid, was collected and dried at room temperature in vacuo over P$_2$O$_5$ for 24 hr., wt. 220 mg (70% yield).

The diazonium fluoroborate derivative (160 mg, 0.59 mmol) was suspended in 25 ml of a mixture of dry xylenes and heated under reflux for 3 hr. The cooled suspension was filtered and the filtrate, which showed the presence of three products, including 4-fluoroestra-1,3,5(10)-trien-17-beta-ol, by TLC analysis using 100% dichloromethane, was evaporated to dryness. The residue was subjected to preparative TLC using the same solvent system and the desired product, 4-fluoroestra-1,3,5(10)-trien-17$\beta$-ol, was isolated as a foam (wt. 60 mg, 37% yield). The latter, on (mass and $^1$H NMR) spectral analyses, was identical in all respects with a sample obtained from a corresponding 3-O-(1-phenyl-1H-tetrazol-5-yl) ether.

EXAMPLE 5

4-Nitroestra-1,3,5(10)-trien-17-beta-ol

To a stirred solution of MCPBA (518 mg, 3 mmol) in dry CH$_2$Cl$_2$ (10 mL) was slowly added, under gentle reflux and an atmosphere of argon, a solution of 4-aminoestra-1,3,5(10)-trien-17-beta-ol (136 mg, 0.5 mmol) in CH$_2$Cl$_2$ (3 mL). After all the amino compound was added, the reaction mixture was cooled immediately to room temperature and was washed successively with 10% aqueous Na$_2$SO$_3$ (2×10 mL), a saturated solution of NaHCO$_3$ (2×10 mL) and water (2×15 mL). The dried (NaSO$_4$) organic fraction was evaporated and the residue (140 mg) subjected to flash chromatography (SiO$_2$/S$_1$). The product, a yellow solid (85 mg, 56% yield), was crystallized from ether-petroleum ether (30°-60° C.) to provide the analytical sample, mp 151°-152° C.; IR(KBr): 3400, 2920, 2850, 1515, 1340, 1130, 1070, 1045 cm$^{-1}$, $^1$H NMR $\delta$0.82 (s, 3H), 1.3–2.36 (m, 15H), 3.74 (t, 1H) 7.28 (d, J=15.9 Hz, 1H), 7.57 (d, J=8.1 Hz, 1H), 7.64 (d, J=8.1 Hz, 1H); mass spectrum m/z 301 M+.

Anal. Calc'd for C$_{18}$H$_{23}$NO$_3$: C, 71.73; H, 7.69; N, 4.65. Found, C, 71.59; H, 7.69; N, 4.65.

EXAMPLE 6

2-Nitroestrone 3-O-(Trifluoromethyl)-sulfonate

A well-stirred suspension of 2-nitroestrone (3.15 g, 10 mmol), Dannenberg et al., *Hoppe-Segler's Z. Physiol. Chem.*, 348:775 (1967), in dry acetone (100 mL) containing triethylamine (2.1 mL, 15 mmol) was treated with trifluoromethyl sulfonyl chloride (1.6 mL, 15 mmol) under argon as described in Example 1. The reaction product was flash chromatographed on SiO$_2$ (S$_3$) to give a pale yellow solid (4.2 g, 96% yield) which crystallized from isopropanol in the form of pale yellow needles, mp 154°-155° C.; IR (KBr): 1740, 1530, 1435, 1345, 1215, 1140, 1050, 1035 cm$^{-1}$, $^1$H NMR $\delta$0.94 (s, 3H), 1.18–3.11 (m, 15H), 7.14 (s, 1H), 8.10 (s, 1H).

Anal. Calc'd for C$_{19}$H$_{20}$F$_3$NO$_6$S.0.25 C$_3$H$_8$O: C, 51.29; H, 4.80; F, 12.33; N, 3.03; S, 6.93. Found: C, 51.60; H, 4.56; F, 12.16; N, 3.00; S, 6.55.

EXAMPLE 7

2-Nitroestra-1,3,5(10)-triene-3,17-beta-diol 3-O-(Trifluoromethyl)sulfonate

Reduction of 2-nitroestrone 3-O-(trifluoromethyl)-sulfonate (4.47 g, 10 mmol) in toluene (75 mL) containing hexadecyltributylphosphonium bromide (508 mg, 1 mmol) with NaBH$_4$ (1.13 g, 30 mmol) in H$_2$O (8 mL) was carried out as in Example 2. The product, after flash chromatography on SiO$_2$ (S$_2$)$_7$ was obtained in the form of a foam (4.20 g. 93% yield); IR(KBr): 3400, 2920, 1520, 1420, 1340, 1205, 1130 cm$^{-1}$; $^1$H NMR $\delta$0.80 (s, 3H), 1.17–3.03 (m), 3.76 (t, J=6.15 Hz, 1H) 7.10 (s, 1h), 7.26 (s, 1H).

Anal. Calculated for C$_{19}$H$_{22}$F$_3$NO$_6$S.C$_4$H$_{10}$O: C, C, 52.76; H, 5.91; F, 10.89; N, 2.68; S, 6.12. Found: C, 53.29; H, 5.91; F, 10.89; N, 2.68; S, 6.12.

EXAMPLE 8

2-Aminoestra-1,3,5(10)-trien-17-beta-ol

Reduction of 2-nitroestra-1,3,5(10)-triene-3,17-beta-diol 3-O-(trifluoromethyl)-sulfonate (3.48 g, 7.7 mmol) in EtOH (100 mL) containing triethylamine (1.1 mL, 7.7 mmol), 10% Pd/C (0.848 g, 0.8 gatom Pd) and at 16 psi of H$_2$ for 5 h was carried out as described in Example 3. The reaction mixture gave a crude product (1.92 g), which crystallized from CH$_2$Cl$_2$-hexane as a colorless solid, (1.43 g, 68% yield), mp 178°-180° C. (dec), IR(KBr) 3420, 3365, 2900, 1610, 1500, 1445, 1335, 1265, 1215, 1135, 1055 cm$^{-1}$; $^1$H NMR δ0.77 (s, 3H) 1.06–2.81 (m), 3.72 (t, J=8.2 Hz, 7.91 Hz, 1H), 6.48 (d, J=8.06 Hz, 1H) 6.65 (s, 1H), 6.87 (d J=7.91, 1H).

Anal. Calc'd for $C_{18}H_{25}NO$: C, 79.66; H, 9.28; N, 5.19. Found: C, 79.44; H, 9.16; N, 4.96.

EXAMPLE 9

2-Aminoestra-1,3,5(10)-trien-17-beta-ol

To a well-stirred solution of 2-aminoestra-1,3,5(10)-trien-17-beta-ol (543 mg, 2 mmol) in a mixture of 48% $HBF_4$ (3.0 mL, 16 mmol), THF (3 mL) and dioxane (0.5 mL) was added under the solution surface, via a syringe, a cold solution of $NaNO_2$ (76 mg, 4 mmol) with external cooling. The temperature was then allowed to rise to −5° to 0° C. an stirring was continued for 1h. Cold water (20 mL) was added. This led to the deposition of a yellow precipitate. Stirring was continued for an additional h at −5° to 0° C., after which the reaction mixture was extracted with $CH_2Cl_2$ (3×15 mL). The organic layer was washed with $NaHCO_3$ (3×10 mL), then dried ($Na_2SO_4$) and concentrated to yield 590 mg (80% yield) of a reddish solid, mp 63°–70° C. (dec);, IR(KBr): 3420, 2920, 2860, 2260 1630, 1050 cm$^{-1}$.

A suspension of the diazonium salt (580 mg, 1.57 mmol) in xylene (50 mL) was heated under reflux for 18 h. The cooled, supernatant fraction was decanted and the process was repeated with refluxing xylene (3×50 mL) carried out for 3 h periods. The combined xylene extracts were concentrated to an oil which TLC ($S_1$) showed to be a mixture of products. The mixture was subjected to repeated (3) flash chromatography ($SiO_2$, $S_1$) which gave a solid that was characterized as a single spot on TLC ($S_1$). Two recrystallizations of this material from hexane gave an off-white product in the form of compact needles (69 mg, 16% yield), mp 124°–126° C., IR(KBr): 3300, 2940, 2910, 2850, 1610, 1580, 1390, 1260, 1130, 1050 cm$^{-1}$; $^1$H NMR δ0.78 (s, 3H), 0.93–3.73 (m, 16H), 6.80 (m, 3H).

Anal. Calc'd for $C_{18}H_{23}FO$: C, 78.79; H, 8.45; F, 6.92. Found: C, 78.74; H, 8.50; F, 7.03.

EXAMPLE 10

2-Nitroestra-1,3,5(10)-trien-17-beta-ol

The oxidation of 2-aminoestra-1,3,5(10)-trien-17-beta-ol (136 mg, 0.5 mmol) in $CH_2Cl_2$ (7.5 mL) with MCPBA (518 mg, 3 mmol) in $CH_2Cl_2$ (5 mL) was carried out as described in Example 5 to yield a pale yellow foam (110 mg). The latter, on flash chromatography ($SiO_2/S_2$), gave a pale yellow solid (85 mg, 56% yield), mp 165°–167° C.; IR(KBr) 3350, 2900, 1520, 1350, 1060 cm$^{-1}$; $^1$H NMR δ0.79 (s, 3H), 1.17–3.01 (m, 15H) 3.76 (t, J=7.62, 8.49 Hz, 1H), 7.19 (d, J=8.5 Hz, 1H) 7.92 (d, J=8.35 Hz, 1H), 8.13 (s, 1H); Mass spectrum m/z 301 M+.

Anal. Calc'd for $C_{18}H_{23}NO_3$: C, 71.73; H, 7.69; N, 4.65. Found: C, 71.49; H, 7.47; N, 4.41.

EXAMPLE 11

Effects of 4-Nitroestrone 3-Methyl Ether (ST; Y-NO$_2$, Z=OMe, R$_1$+R$_2$=O) on Mammary Tumors Induced by Dimethylbenz(a)anthracene Chemicals and Reagents. Estrone, 17-beta-estradiol 3-benzoate, estrone sulfate, aryl sulfatase (EC 3.1.6.1), beta-glucuronidase (EC3.2.1.31), 7,12-dimethylbenz(a)anthracene (DMBA), and 5-fluorouracil were obtained from Sigma Chemical Co. (St. Louis, Mo.). 4-Nitroestrone 3-methyl ether, 4-nitroestrone, and 2,4-dinitroestrone were synthesized by the procedures of Tomson et al., supra.

Animals. Virgin female Sprague-Dawley rats (The Charles River Co., Wilmington, Mass.) were housed 4 to 6/cage in a light (12 hr/day)—and temperature (24°)—controlled room and given a diet of Wayne Lab-Blox laboratory chow (Allied Mills, Inc., Chicago, Ill.) and tap water ad libitum. At 50 days of age, rats were intubated with DMBA (10 mg/100 g body weight) dissolved in sesame oil (20 mg/ml). Beginning at Day 45 after intubation, all animals were weighed and palpated once per week. Tumor volumes were calculated by measuring 2 diameters with a caliper and the third dimension with a ruler, then by substituting values:

$$\text{Volume (cu cm)} = \pi 1/6 \, abc$$

where a, b, and c are the 3 different diameters of the tumor. The agreement of the in vivo tumor volume and measurements of excised tumors identified at necropsy was 95 to 99%. When about 75% of rats had palpable tumors (81 to 92 days after intubation), the animals were randomized, excluding rats with tumors larger than 2.00 ml and rats with more than 5 tumors/animal. The mean initial tumor volumes in control and treated groups ranged between 0.4 and 0.9 cu cm over the various experiments. When necessary, ovariectomy (ether anesthesia) was performed on the first or second day after the initiation of the study. The significance of difference between treatment groups was examined by Student's t test.

Estrogen derivatives (>99% pure by thin-layer chromatography) were injected s.c. daily (Monday to Friday). After distribution in SSV (steroid-suspending vehicles, 0.9% NaCl solution with 0.5% sodium carboxymethyl-cellulose-7, 0.4% polysorbate; and 0.9% benzylalcohol, obtained from the National Cancer Institute), the steroids (20 mg/ml) were administered at 0.12 to 54 mg/kg body weight. The suspension was sonicated before use to achieve uniform distribution. 17-Beta-estradiol 3-benzoate was dissolved directly in sesame oil to a concentration of 2.5 mg/ml; 5 fluorouracil was dissolved in water (25 mg/ml). The control group was given injections of SSV or sesame oil alone.

The toxicity of all antitumor agents was determined by comparing body weights of treated and control animals.

Postmortem Examination and Histopathology of Tumors. Rats were selected for colchicine injections (2 mg/kg body weight) 2 hr prior to necropsy to obtain an accurate measurement of mitotic indices of tumors. Animals were sacrificed with $CO_2$ gas or bled to death via the abdominal aorta. Tumors and tissues were removed and preserved in 10% neutral buffered formalin for histopathological examination. Gross anomalies of abdominal, thoracic, and cranial cavities were recorded. Uteri were removed, trimmed, and weighed fresh. Ovaries, adrenals, and pituitaries were trimmed and weighed after fixation.

Histopathological observations on hematoxylin-and iosin-stained tumor and organ sections were performed, and comparisons between the control and treated groups were carried out using computer analysis. The microscopic parameters used to judge the degree of anaplasia in DMBA-induced mammary neoplasms, when treated animals were compared to controls, were: (a) the type of epithelium or mammary tissue involved; (b) the degree of encapsulation of the neoplasm; (c) the number of mitotic figures observed; (d) the extent of stroma invasions of the neoplastic epithelium; (e) the severity of lymphocytic infiltration of the neoplasms; and (f) the regressive, degenerative, or vacuolative changes in the neoplastic epithelium. These criteria are suggested by Boylan et al., "Morphology, growth characteristics and estrogen binding capacity of DMBA-induced mammary tumors from ovariectomized rats," *Br. J. Cancer*, 35:602–609 (1977); Gullino et al., "Physiopathological characteristics of hormone dependent tissue," *J. Natl. Cancer Inst.*, 49:1333–1348 (1972); Haslam et al., "Histopathogenesis of 7,12-dimethylbenz(a)anthracene induced rat mammary tumors," *Proc. Natl. Acad. Sci U.S.A.*, 74:4020–4024 (1977); Russo, "Pathogenesis of mammary carcinomas induced in rats by 7,12-dimethylbenz(a)anthracene," *J. Natl. Cancer Inst.*, 49:435–445 (1977) and Strettony et al., "Spontaneous regression of induced mammary tumors in rats," *Br. J. Cancer*, 17:85–89 (1973). Histological examination was performed on all mammary tumors.

Results

In a series of tests using 7-10 Sprague-Dawley rats/group, subcutaneous injections of 24 mg/kg of body weight of an estrogen analog being evaluated were given for 35 days. The estrogen analogs selected were known to be superior estrogen sulfotransferase inhibitors, Rozhin et al., *J. Biol. Chem.*, 252:7214–7220 (1977).

In Table I below, the mean values are the mean ±S.D. The following results were obtained:

TABLE I

| Estrogen analog injected | Mean tumor volume (cu cm) | Mean tumor no. (no. tumors/rat) |
|---|---|---|
| None | 1.48 ± 2.09 | 3.30 ± 2.60 |
| 2,4-Dibromoestrone 3-methyl ether | 1.24 ± 1.07 | 4.26 ± 2.51 |
| 2,4-Dinitroestrone | 1.14 ± 1.37 | 2.90 ± 1.67 |
| 4-Nitroestrone | 0.75 ± 0.10 | 1.95 ± 2.60 |
| 4-Nitroestrone 3-methyl ether | 0.05 ± 0.05 | 1.35 ± 0.40 |

In the table p values, when compared to those of the control tumors, were <0.05. The results for the 2,4-dibromoestrone 3-methyl ether, 2,4-dinitroestrone, and 4-nitroestrone treatments were therefore insignificant.

EXAMPLE 12

Effects of 4-Nitroestra-1,3,5(10)-trien-17-beta-ol (ST; Y=NO$_2$, Z=H, R$_1$=beta-OH, R$_2$=H) on Mammary Tumors Induced by Dimethylbenz(a)anthracene The compound of Example 5 was suspended in a mixture of 3% by weight of polyethoxylated castor oil, 3% by weight of ethanol and 94% by weight of water.

The test compound was injected subcutaneously into mice in which DMBA mammary tumors had been induced as in Example 11. Controls received subcutaneous injections of the suspending medium.

As shown in Table II, 4-nitroestra-1,3,5(10)-trien-17-beta-ol inhibited the growth of MXT mouse mammary ductal carcinoma.

TABLE II

| Subcutaneous Treatment of Early Stage, Hormone-Dependent MXT Mouse Mammary Ductal Carcinoma | | |
|---|---|---|
|  | Control | 4-Nitroestra-1,3,5(10)-trien-17-beta-ol |
| (s.c.) Dosage (mg/kg) | — | 200 |
| Schedule | — | QD 1-19 |

TABLE II-continued

| Subcutaneous Treatment of Early Stage, Hormone-Dependent MXT Mouse Mammary Ductal Carcinoma | | |
|---|---|---|
|  | Control | 4-Nitroestra-1,3,5(10)-trien-17-beta-ol |
| Time for Median Tumor to Reach 500 mg | 18 | 45 |
| T/C Value Day 39 (%) | — | 8.2 |

EXAMPLE 13

Evaluation of 2- or 4-Substituted-estra-1,3,5(10)-trien-17-beta-ols as Estrogen Sulfotransferase Inhibitors Compounds prepared in the foregoing examples were evaluated as inhibitors of porcine estrogen sulfotransferase as taught by Rozhin et al., *J. Biol. Chem.*, 252:7214–7220 (1977) and Brooks et al., U.S. Pat. No. 4,496,555.

As shown by the results in Table III, all of the 2- and 4-substituted estra-1,3,5(10)-trien-17-beta-ols were more active than the unsubstituted compound. The most active compound was 4-nitro-estra-1,3,5(10)-trien-17-beta-ol.

TABLE III

| Inhibition of Porcine Endometrial Estrogen Sulfotransferase by Estra-1,3,5(10)-trien-17-beta-ols | |
|---|---|
| Substituted Estra-1,3,5(10)-trien-17-beta-ol | Apparent Ki (uM) |
| 4-nitro | 2.43 ± 0.16 |
| 2-amino | 7.51 ± 1.63 |
| 2-nitro | 9.76 ± 1.18 |
| 4-fluoro | 10.20 ± 0.76 |
| 4-amino | 11.90 ± 0.56 |
| 2-fluoro | 13.60 ± 2.9 |
| (unsubstituted) | 16.30 ± 3.9 |

EXAMPLE 14

Preparation of a Longlasting Troche

Troches (1500), each weighing 750 mg, were formulated as follows:

| Ingredient | Grams |
|---|---|
| (a) 4-Nitroestra-1,3,5,(10)-trien-17-beta-ol | 15.0 |
| (b) Pectin | 370.0 |
| (c) Gelatin | 370.0 |
| (d) Sodium carboxymethylcellulose | 370.0 |

The diol was mixed with approximately 10 gm. of pectin. The remainder of the pectin and other ingredients were added and mixed thoroughly. The resulting mixture was compressed into capsule-shaped troches, each of which contained 10 mg of 4-nitroestra-1,3,5(10)-trien-17-beta-ol.

EXAMPLE 15

Preparation of a Hard Candy Lozenge

The following formulation can be used to prepare approximately 9,000 lozenges weighing 5.0 grams each.

| Ingredient | Weight |
|---|---|
| (a) 4-Nitroestra-1,3,5(10)-trien-17-beta-ol | 90 gms. |
|  | 450 gms. |
| (c) Saccharin sodium | 45 gms. |
| (d) Cetyl diethyl benzyl-ammonium chloride | 27 gms. |
| (e) Benzocaine | 45 gms. |
| (f) Granular sugar | 28 gms. |
| (g) Liquid glucose (43°) | 16.7 kgs. |
| (h) Sour orange flavor q.s. Wild cherry flavor q.s. | |

The granular sugar is placed into a pre-cook kettle with 14 liters of water. The mixture is brought to a boil and the sodium cyclamate is added and dissolved with stirring. Glucose is added and the mixture brought to a predetermined temperature of 135° C.

The composition is transferred to a continuous vacuum cooker and reduced to a proper consistency for a candy base, to which the remaining ingredients are added with stirring. The mixture is thoroughly kneaded and a continuous rope formed. Lozenges weighing about 5.0 gm. each and containing about 10.0 mg. of the active compound are cut from the rope, packaged and distributed in any convenient manner.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

We claim:

1. A method for inhibiting the growth of MXT murine ductal carcinoma comprising administering to mice being treated a compound of the formula

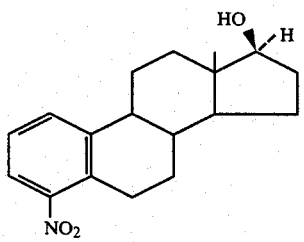

in admixture with a pharmacologically and physiologically acceptable carrier, in an amount sufficient to inhibit the growth of the ductal carcinoma.

2. The method of claim 1, wherein the compound is administered subcutaneously.

3. A process for the synthesis of 2- or 4-substituted estra-1,3,5(10)-trien-17-beta-ol compounds by the steps of:
   (a) converting a 2- or 4-nitroestrone precursor to a corresponding 2- or 4-nitroestrone 3-O-(trifluoromethyl)sulfonate by reaction with a trifluoromethanesulfonyl halide;
   (b) reducing the thus-formed 2- or 4-nitroestrone 3-O-(trifluoromethyl)sulfonate with sodium borohydride in the presence of a phase transfer agent to a corresponding 2- or 4-nitroestra-1,3,5(10)-trien-3,17-beta-diol 3-O-(trifluoromethyl)sulfonate;
   (c) converting the thus-produced 2- or 4-nitroestra-1,3,5,(10)-trien-3,17-beta-diol 3-O-(trifluorormethyl)sulfonate to a corresponding 2- or 4-aminoestra-1,3,5(10)-trien-17-beta-ol by hydrogenation in the presence of a catalyst and, when the 2- or 4-substituent is other than amino, including the further step of:
   (d) converting the thus-formed 2- or 4-aminoestra-1,3,5(10)-trien-17-beta-ol by a Sandmeyer conversion of formation and decomposition of a diazonium salt therefrom to a corresponding 2- or 4-haloestra-1,3,5(10)-trien-17-beta-ol or
   (e) converting the thus-formed 2- or 4-aminoestra-1,3,5(10)-trien-17-beta-ol to a 2- or 4-nitroestra-1,3,5(10)-trien-17-beta-ol by oxidation with meta-chloroperbenzoic acid.

4. The process of claim 3, wherein the phase transfer agent is hexadecyltributyl phosphonium bromide.

5. The process of claim 3, wherein the 2- or 4-nitroestra-1,3,5(10)-trien-3,17-beta-diol 3-O-(trifluoromethyl)-sulfonate is hydrogenated in the presence of palladium on carbon catalyst.

6. The process of claim 3 in 2- or 4-aminoestra-1,3,5(10)-trien-17-beta-ol is treated with fluoboric acid and sodium nitrite and a resulting 2- or 4-diazonium fluoroborate is decomposed to produce 2- or 4-fluoroestra-1,3,5(10)-trien-17-beta-ol.

7. The process of claim 3, wherein 2- or 4-aminoestra-1,3,5(10)-trien-17-beta-ol is treated with sodium nitrite and hydrochloric, hydrobromic or hydriodic acid to produce a corresponding 2- or 4-diazonium halide and the thus-produced diazonium halide is treated with a cuprous halide to produce 2- or 4-chloro-, bromo- or iodoestra-1,3,5(10)-trien-17-beta-ol.

* * * * *